(12) United States Patent
Batenburg et al.

(10) Patent No.: US 7,923,435 B2
(45) Date of Patent: Apr. 12, 2011

(54) *HOODIA* PLANT EXTRACT WITH IMPROVED FLAVOR

(75) Inventors: Amir Maximiliaan Batenburg, Vlaardingen (NL); Mohamed Said Chaara, Vlaardingen (NL); Egge Aart Eddy Rosing, Vlaardingen (NL); Frederik Michiel Meeuse, Vlaardingen (NL); Salomon Leendert Abrahamse, Vlaardingen (NL)

(73) Assignee: Phytopharm PLC, Cambridge (GB)

( * ) Notice: Subject to any disclaimer, the term of this patent is extended or adjusted under 35 U.S.C. 154(b) by 302 days.

(21) Appl. No.: 12/148,631

(22) Filed: Apr. 21, 2008

(65) Prior Publication Data

US 2009/0264376 A1 Oct. 22, 2009

(51) Int. Cl.
*A01N 43/04* (2006.01)
*A61K 31/70* (2006.01)

(52) U.S. Cl. ............................... 514/33; 514/34

(58) Field of Classification Search ............ None
See application file for complete search history.

(56) References Cited

U.S. PATENT DOCUMENTS

| | | | |
|---|---|---|---|
| 4,562,250 A | 12/1985 | Staba et al. | 536/6 |
| 6,376,657 B1 * | 4/2002 | Van Heerden et al. | 536/5 |
| 6,635,490 B1 | 10/2003 | Fu et al. | 436/94 |
| 6,670,459 B2 | 12/2003 | Handa et al. | 536/5 |
| 7,008,648 B2 | 3/2006 | Corley et al. | 424/725 |
| 7,265,101 B2 | 9/2007 | Raskin et al. | 514/170 |
| 2002/0146468 A1 | 10/2002 | Rubin et al. | 424/725 |
| 2004/0082521 A1 | 4/2004 | Singh | 514/26 |
| 2006/0051435 A1 * | 3/2006 | Udell et al. | 424/725 |
| 2007/0104805 A1 | 5/2007 | Udell | 424/725 |
| 2007/0196436 A1 | 8/2007 | Abrahamse et al. | 424/439 |
| 2008/0044552 A1 | 2/2008 | Alaoui Ismaili et al. | 426/655 |

FOREIGN PATENT DOCUMENTS

| | | |
|---|---|---|
| CN | 1803827 | 7/2006 |
| DE | 10 2006 024 885 | 11/2007 |
| EP | 1 897 449 | 3/2008 |
| WO | 2005/116049 | 12/2005 |
| WO | 2006/051334 | 5/2006 |
| WO | 2007/096239 | 8/2007 |
| WO | 2007/144347 | 12/2007 |
| WO | 2008/019920 | 2/2008 |
| WO | 2008/022875 | 2/2008 |
| WO | 2008/028584 | 3/2008 |

OTHER PUBLICATIONS

Pawar et al. Steroids (2007), vol. 72, pp. 881-891.*
Pawar et al. Steroids (2007), vol. 72, pp. 524-534.*
Co-pending Application: Applicant: Povey et al., Filed: Apr. 21, 2008.
Derwent Abtract of CN 1803827—published Jul. 19, 2006.
European Search Report in an EP application EP 09 15 6597.
Janssen et al. "Quantification of appetite suppressing steroid glycosides from *Hoodia gordonii* in dried plant material, purified extracts and food products using HPLC-UV and HPLC-MS Methods", Analytica Chimica Acta, vol. 617, 2008, pp. 200-207.

* cited by examiner

*Primary Examiner* — Patrick T Lewis
(74) *Attorney, Agent, or Firm* — Harness, Dickey & Pierce, P.L.C.; J. Timothy Keane; Kisuk Lee

(57) ABSTRACT

Extracts of *Hoodia* plant containing steroidal glycosides which have improved flavor, by virtue of reduced levels of discovered negative flavor compounds. Food compositions containing steroidal glycosides with reduced amounts of discovered negative flavor components are also included.

21 Claims, No Drawings

HOODIA PLANT EXTRACT WITH IMPROVED FLAVOR

TECHNICAL FIELD

The present invention relates to plant extracts of the plants of the *Hoodia* family.

BACKGROUND OF THE INVENTION

Extracts obtainable from plants of *Hoodia* genus (formerly the *Hoodia* and *Trichocaulon* genera) have been shown to have an appetite suppressant activity and are potentially useful in weight management products. U.S. Pat. No. 6,376,657 discloses that these plants contain steroidal glycosides and also discloses processes to extract steroidal glycosides from *Hoodia* plants. Compositions comprising *Hoodia* extract have also been described, for example, by US2007196436 (Abrahamse et al.), US2002146468 (Rubin et al.). A number of documents also described extracting steroidal glycosides from plant material and some also include further purifying/concentrating the obtained extract. See for instance US2008044552 (Ismaili et al.), WO 08/028584, WO 05/116049, DE 102006024885, US2007104805 (Udell), U.S. Pat. No. 7,265,101 ((Raskin et al.), WO06/0051334, US20040082521, U.S. Pat. No. 7,008,648 (Corley et al.), U.S. Pat. No. 6,670,459 (Handa et al.), U.S. Pat. No. 6,635,490 (Fu et al.), U.S. Pat. No. 4,562,250 (Staba et al.), CN 1803827.

The present invention is based at least in part on the discovery that it is difficult to formulate food products comprising *Hoodia* extracts, because the extracts have a characteristic, thoroughly unpleasant smell, which also detrimentally impacts the taste of the extract. In the food industry, a flavor is defined as the combination of smelt and taste. Accordingly, there is a need for *Hoodia* plant extracts of improved flavor.

SUMMARY OF THE INVENTION

Among hundreds of compounds present in the complicated mixture of organic compounds in a plant extract, the inventors discovered the primary and secondary compounds responsible for negative flavors within the *Hoodia* plant extract. The present invention is based, at least in part, on the identification of primary and secondary negative flavors, and the also identifying and quantifying compounds responsible for these negative flavors in *Hoodia* plant extracts; when the levels of these negative flavor compounds are reduced, improved flavor is obtained.

The invention includes *Hoodia* extracts with reduced levels of negative flavor compounds. The invention also includes edible compositions comprising *Hoodia* steroidal glycosides and reduced levels of negative flavor compounds.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Steroidal glycoside" as used herein means a steroid (four fused rings in a 6-6-6-5 pattern), further comprising at least one side group substitution which is a glycoside (a molecule in which a sugar group is bonded through its anomeric carbon to another group via an O-glycosidic bond), preferably a deoxy or di-deoxy glycoside, and another side group comprising a carbonyl (—C=O) group, preferably located on the 5-membered ring and most preferably further comprising a tigloyl group

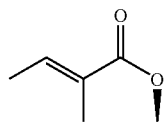

on carbon number 12.

Initial *Hoodia* Plant Extracts

The steroidal glycoside in the present invention is delivered to food compositions from the improved flavor extracts of plants of the *Hoodia* (also known as *Trichocaulon*) genus. The improved flavor extracts are obtained by removing negative flavor compounds from the initial plant extracts. More preferably, the initial plant extract is selected from the group consisting of *Trichocaulon piliferum* extracts, *Trichocaulon officinale* extracts, *Hoodia currorii* extracts, *Hoodia Gordonii* extracts, *Hoodia lugardii* extracts and mixtures thereof. *Hoodia Gordonii* extracts are the most preferred due to the clinically proven safety of use and efficacy in appetite suppression.

The plant extracts are preferably of certain minimum purity in order to obtain best efficacy at minimum cost. According to the present invention the extract typically comprises at least 10% of steroidal glycosides, by weight of the extract, preferably at least 25% of steroidal glycosides, more preferably at least 50%, most preferably at least 75% and optimally at least 80%, generally up to 99%, calculated on the dried final product. U.S. Pat. No. 6,376,657, incorporated by reference herein, describes the preparation of an extract comprising steroidal glycosides from the genus *Hoodia*, having appetite suppressant activity. The solvents specifically mentioned to perform the extraction are one or more of methylene chloride (dichloromethane), water, methanol, hexane, ethyl acetate or mixtures thereof. An alternative method to obtain an extract is disclosed by separating plant sap from the plant solid material. Other methods of extracting a steroidal glycoside from plants are also suitable. See for instance a CO2 extraction method described in WO2005/116049, incorporated by reference herein. Solvent extracted forms of the extract are preferred due to higher purity and process efficacy. A preferred solvent extraction method (also known as liquid/liquid extraction) is described in US20080050499, incorporated by reference herein; this method typically achieves relatively high steroidal glycoside content—more than 35%, and typically at least 70%, calculated on the dried final product.

"Extract" as used herein includes solvent-extracted liquid, solid or spray-dried or freeze-dried forms of extracts, sap, which also may be purified, partially purified, concentrated and/or fractionated, or otherwise concentrated plant preparation.

Suitable steroidal glycoside compounds include but are not limited to the general structural formula (1):

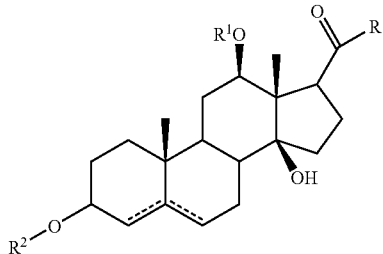
(1)

wherein

R=alkyl;

$R^1$=H, alkyl, tigloyl, benzoyl or any other organic ester group, most preferably to optimize efficacy tigloyl;

$R^2$=H or one or more 6-deoxy carbohydrates, or one or more 2,6-dideoxy carbohydrates, or glucose radical, or combinations thereof; and wherein the broken lines indicate the optional presence of a further bond between carbon atoms C4 and C5 or between carbon atoms C5 and C6.

Particularly preferred steroidal glycosides are analogs of Compound of Formula 1, including Compounds of Formula (2) through Formula (8), and mixtures thereof, since these are obtainable from the preferred *Hoodia* plants.

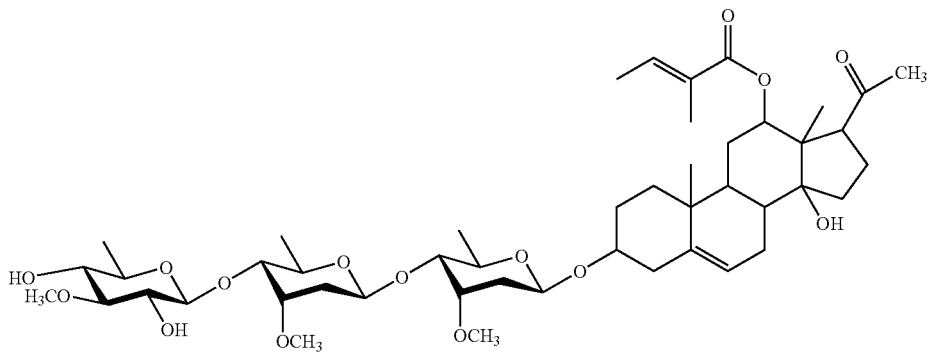
(2)

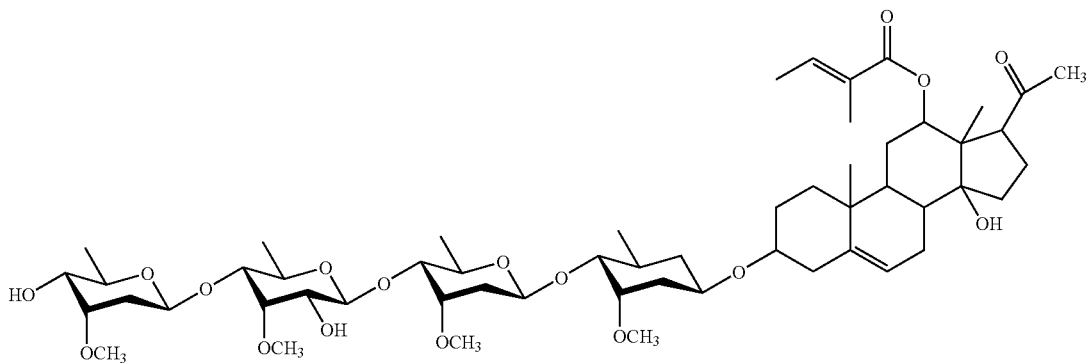
(3)

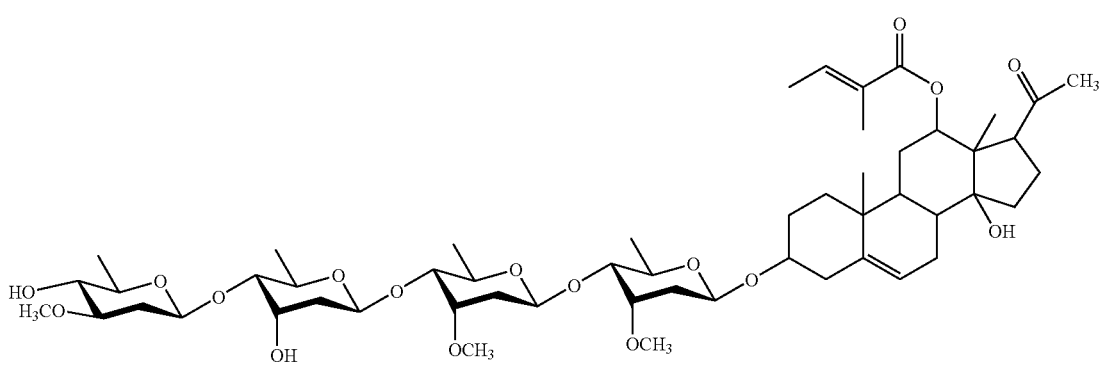
(4)

(5)
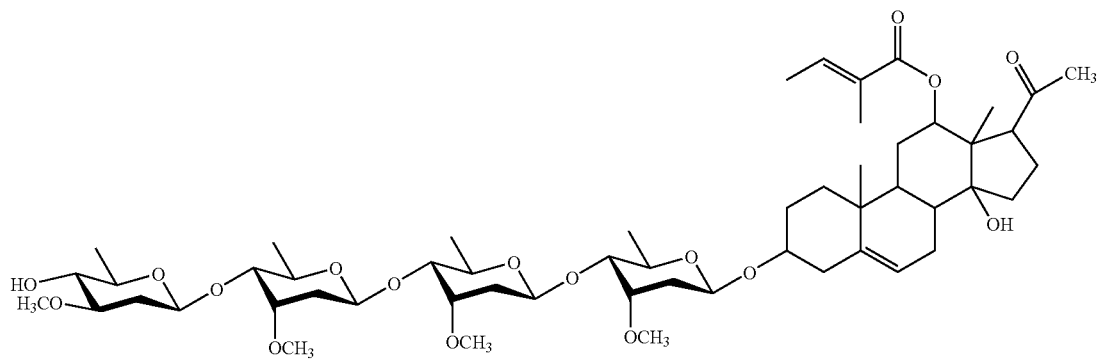
(6)
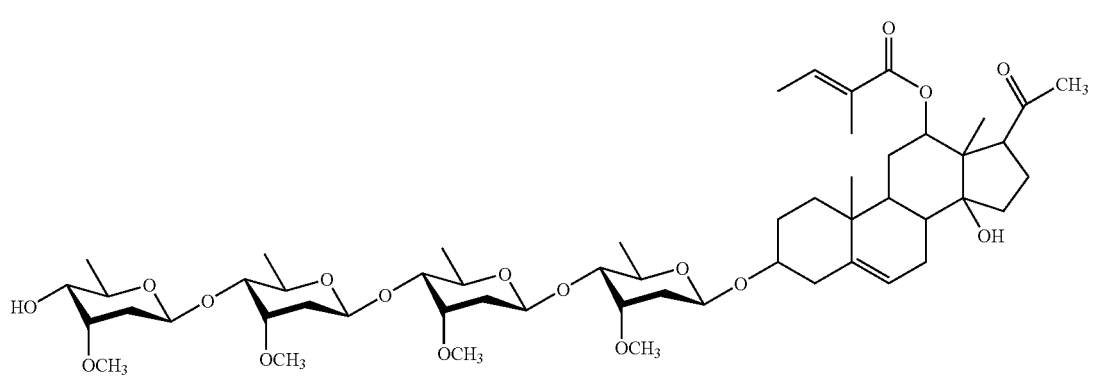
(7)
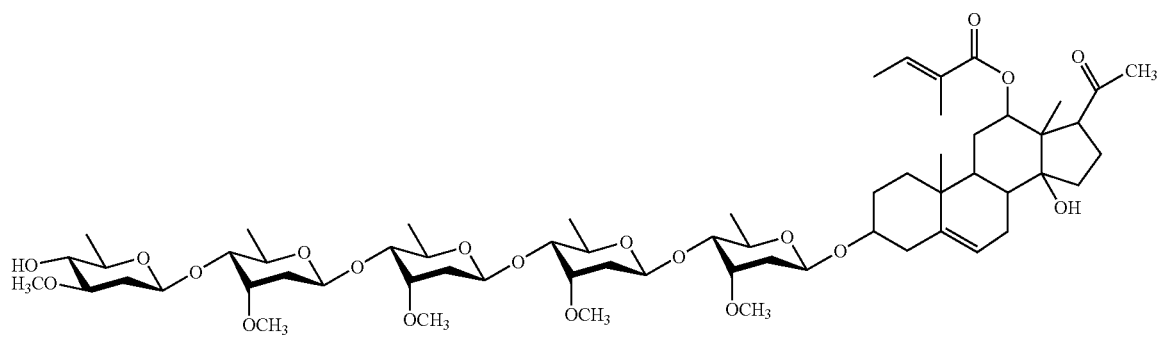
(8)
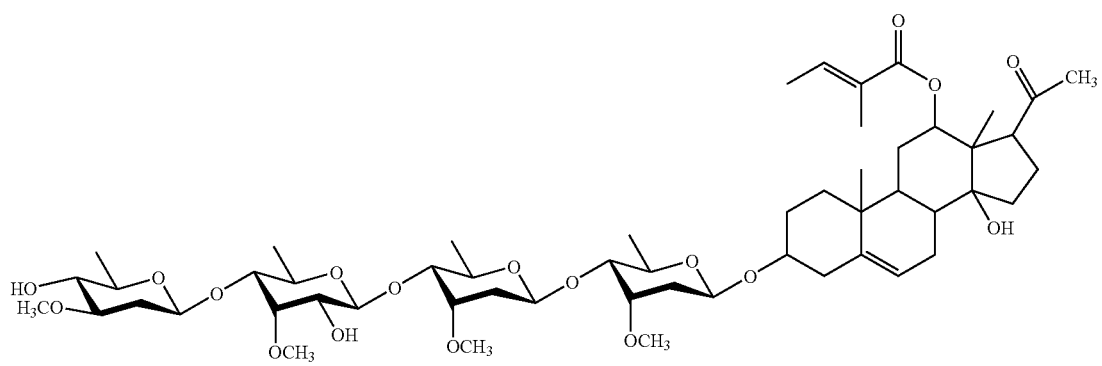

Other steroidal glycosides not specifically mentioned herein may be included in the inventive product. It will be understood that the invention also encompasses isomers, derivatives, salts, esters and analogs of the steroidal glycosides (preferably, biologically active) and mixtures thereof.

Measurement of Steroidal Glycosides

Steroidal glycoside concentrations are determined using high performance liquid chromatography (HPLC) with UV detection after extraction or dissolution.

For *Hoodia* extracts approximately 30 mg of the material is dissolved in 50 ml of methanol by sonication for 10 minutes. After filtration 1 ml of the filtrate is evaporated to dryness and reconstituted in 1 ml acetonitrile/water (50/50 v/v). For the measurements in oil approximately 100 mg of the oil is dissolved in 10 ml THF.

Steroidal glycosides are measured by LC-UV at 220 nm. To this end 20 µl of the extracts are injected onto a Zorbax SB-C8 analytical column of 205×4.6 mm packed with 5 µm particles and equipped with a Zorbax SB-C8 guard column of 12.5×4.6 mm packed with the same stationary phase. For the oil samples an injection volume of 10 µl is used. In all analyses the column system is held at 40° C. Gradient elution is performed starting at 41.2% acetonitrile/methanol (85/15 v/v) and 58.8% water/methanol (85/15 v/v) at a flow rate of 1 ml/min. Initial conditions are held for 10 minutes before the organic solvent fraction is changed to 88.2% acetonitrile/methanol (85/15 v/v) and 11.8% water/methanol (85/15 v/v) over 30 minutes. After a final hold of 5 minutes the system is re-equilibrated to the starting conditions. For the oil samples an adapted gradient is used:

| HPLC gradient for the analysis of Hoodia steroidal glycosides in oil. | | | | |
|---|---|---|---|---|
| Gradient | Time (min) | % water | % acetonitrile | % methanol | Flow (ml/min) |
| 10 min isocratic hold | 0 | 50 | 35 | 15 | 1.0 |
| 30 min linear gradient | 10 | 50 | 35 | 15 | 1.0 |
| 5 min isocratic hold | 40 | 10 | 75 | 15 | 1.0 |
|  | 45 | 10 | 75 | 15 | 1.0 |
|  | 50 | 50 | 35 | 15 | 1.0 |
| Flush | 55 | 1 | 1 | 98 | 2.0 |
|  | 85 | 1 | 1 | 98 | 2.0 |
| Reconditioning | 90 | 50 | 35 | 15 | 1.0 |
|  | 120 | 50 | 35 | 15 | 1.0 |

Compound of Formula 2 of any known purity (92% was used in this case) is used for calibration. Compound 2 may be isolated from an extract of dried *Hoodia Gordonii* using preparative liquid chromatography or may be synthesized (see e.g. U.S. Pat. No. 6,376,657, incorporated by reference herein). A stock solution at 100 µg/ml is prepared in acetonitrile/water (1/1 v/v) and further dilutions are prepared to yield additional calibration standards at 80, 60, 40, 20, 10 and 5 µg/ml. UV response at 220 nm is used for quantification against the Compound 2 calibration line. Relative response factors based on molecular weight are used to quantify the steroidal glycosides against the Compound 2 calibration line. Steroidal glycosides are defined as all peaks eluting between 11 min and the elution time of the compound of Formula 7 plus 2 minutes, that are not present in the blank acetonitrile/water (1/1 v/v) sample nor in a blank oil in case of oil samples. For the compounds of Formula 2-8 the specific relative retention times and response factors, are summarized in the table below.

| Relative retention times and response factors of some steroidal glycosides | | |
|---|---|---|
| Compound | Relative retention time vs. Compound 2 | Response factor vs. Compound 2 |
| formula 2 | 1.000 | 1.000 |
| formula 8 | 1.084 | 1.164 |
| formula 3 | 1.125 | 1.164 |
| formula 4 | 1.193 | 1.130 |
| formula 5 | 1.304 | 1.146 |
| formula 6 | 1.343 | 1.146 |
| formula 7 | 1.422 | 1.309 |

The other steroidal glycosides peaks eluting after 11 minutes have a response factor of 1.081 vs. Compound 2.

Although the above approach for calibration would also work for oil samples (*Hoodia* extract in oil), for these samples usually a different calibration technique is used to allow better compensation for matrix effects. In case of oil samples calibration is performed using a *Hoodia Gordonii* extract previously analysed using the approach given above. A stock solution of approximately 3 mg/ml total *Hoodia Gordonii* actives in THF is used to prepare calibration standards at approximately 0, 0.6, 0.9, 1.2, 1.5, 1.8, 2.1 and 2.5 mg/ml in THF. To 10 ml of each of these standards 100 mg of blank oil is added. Separate calibration lines are calculated for each individual active from the total actives level and the levels of the individual actives in the extract as determined previously. Levels of the actives in unknown samples are obtained from a direct comparison of peak areas of the individual peaks against the appropriate calibration line.

Improved Flavor *Hoodia* Extract

Among hundreds of compounds present in the complicated mixture of organic compounds in a plant extract, the inventors discovered the primary and secondary compounds responsible for negative flavors within the *Hoodia* plant extract. Examples 1 and 2 summarise in greater detail the numerous experiments which ultimately led to the discovery and ranking of the negative flavor compounds.

As part of the present invention, the negative flavor compounds were separated and negative flavors characterised as: cheesy/sweaty, mushroom, medicinal and hay (the hay note being greatly enhanced by a floral note, the latter considered negative according to the present invention). Further, the negative flavor compounds responsible for negative flavors were identified. In addition, the compounds were ranked based on intensity impact (the frequency of flavor detection multiplied by the intensity rating—the rating of at least 35 on the negative flavor qualified the compound as the negative flavor), and/or negative flavor combined with a very high concentration in the initial extract (e.g. 2-methoxy phenol is over-abundantly present in the initial extract), and/or negative flavor combined with extremely low threshold detectable concentration (i.e. very low threshold detection limit makes the compound important in negative flavor compound ranking—e.g., beta-ionone). By far, the negative flavor of highest intensity impact was discovered to be attributable to 3-methyl-butanoic acid, which compound was also discovered to be present in the initial extract in the greatest amount, compared to other negative flavor compounds. Thus, 3-methyl-butanoic acid is the primary negative flavor compound according to the present invention. The secondary negative flavor compounds are 2-methoxy-phenol, beta-ionone, 3-methyl-2,4-nonadione, and 1-octene-3-one.

| Threshold detection limits (μg/kg or parts per billion -ppb) | | | | |
|---|---|---|---|---|
| Compound | Water (Nasal) | Water (Retronasal) | Oil (Nasal) | Oil (Retronasal) |
| 2-methoxy-phenol | 2-21 | 1-13 | 17 | 13 |
| beta-ionone | 0.007-0.5 | | | |
| 3-methylbutanoic acid | 100-1600 | 750 | 22 | 26 |
| 3-methyl-2,4-nonadione | 0.03 | 0.02 | 15-30 | 1.5 |
| 1-octen-3-one | 0.005-1 | 0.01 | 10 | 0.3 |

The concentrations of negative flavor compounds will depend on the concentration of steroidal glycoside, which would differ vastly in the improved flavor extract, and in the food compositions comprising extract. Weight ratio ranges in improved flavor extract or food compositions are as follows:

| NEGATIVE FLAVOR COMPOUND | RANGE | RATIO RANGE (μg compound/ g steroidal glycosides) |
|---|---|---|
| 3-methylbutanoic acid | General | 0-60 |
| | Preferred | 0-20 |
| | Most Preferred | 0-10 |
| | Optimum | 0-2.5 |
| 2-methoxy phenol | General | 0-0.5 |
| | Preferred | 0-0.3 |
| | Most Preferred | 0-0.2 |
| | Optimum | 0-0.1 |
| Beta-ionone | General | 0-0.3 |
| | Preferred | 0-0.1 |
| | Most Preferred | 0-0.05 |
| 3-methyl-2,4-nonadione | General | 0-0.2 |
| | Preferred | 0-0.1 |
| | Most Preferred | 0-0.05 |
| 1-octene-3-one | General | 0-8 |
| | Preferred | 0-3 |
| | Most Preferred | 0-1 |

The preferred improved flavor extract has both 3-methylbutanoic and 2-methoxyphenol at the reduced levels as indicated above, more preferably 3-methylbutanoic acid and 2-methoxyphenol and beta-ionone are all three at the reduced levels, and most preferably all of the negative flavors are at the levels indicated above. The negative flavor compounds are measured as described in Example 2.

Steroidal glycoside concentration in the improved flavor extracts is at least 10% of steroidal glycosides, by weight of the extract, preferably at least 25% of steroidal glycosides, more preferably at least 50%, most preferably at least 75% and optimally at least 80%, generally up to 99%—these steroidal glycoside concentrations are based on the extract, not the extract dissolved in oil.

Process of Obtaining Improved Flavor Extracts

The flavor of the initial *Hoodia* plant extracts may be improved by substantially reducing or eliminating the primary and secondary negative flavor compounds in the extracts. To be acceptable on the commercial industrial scale, the method involves evaporation of the negative flavor compounds by distillation of the solution of the initial *Hoodia* extract in a non-volatile solvent (non-volatile under temperature and pressure conditions described below), most preferably a stripping process which employs gas stream (steam, nitrogen or any other non-reacting gas). "Dissolved" or "Solution" as used herein means forming a single phase when a mixture is visibly examined.

The preferred process is distillation under vacuum at temperatures in the range of 80 to 180° C., preferably 90 to 140° C., more preferably 100 to 140° C., most preferably 100 to 130° C., optimally at 110 to 130° C., since it is most commercially suitable and also results in the reduction or removal of all (primary and secondary) negative flavor compounds. Removal of beta-ionone, 3-methyl-2,4-nonadione and 1-octene-3-one is especially impacted by temperature, with temperatures in the range of 100 to 140° C. more preferred, achieving more preferred ranges of these negative flavor compounds.

The pressure is typically in the range of from 1 and 20 mbar, preferably between 2 and 10 mbar. Lower pressures are economically unattractive; with higher pressures the negative flavor removal becomes less efficient. In a preferred process, in order to attain optimum removal of especially the secondary negative flavor compounds, during the heating time, stripping is employed—the heated solution is flushed, under vacuum, with steam or nitrogen or any other gas that would not react with the system. Steam is preferred with from 0.1% to 2.0% steam, preferably from 0.5% to 1.0%.

A further advantage of the preferred process, at the preferred temperatures, is that this is accomplished while substantially preserving the concentration of steroidal glycosides—the obtained improved flavor extract contains at least 75% of the initial steroidal glycoside concentration, preferably at least 85%, most preferably at least 90% (individual steroidal glycoside content, calculated on dry matter, of individual steroidal glycosides of Formula 2-8, and the average of the total content of the steroidal glycosides).

According to the preferred process, the initial *Hoodia* plant extract is dissolved in oil. The initial *Hoodia* plant extract could be in the form of the end-product of the initial extraction—i.e. powder, where solvent has been removed. Alternatively, in the preferred embodiment of the process, the drying step of the initial *Hoodia* extraction process is eliminated—the *Hoodia* soft extract, still dissolved in the final solvent (or some part thereof) is mixed with the oil. Then residual solvent is evaporated during distillation, which is then followed by stripping to remove the negative flavor compounds.

A preferred solvent is food-grade oil, to optimise the ease of incorporation of improved flavor extract into the inventive food compositions. The solution of *Hoodia* extract in the oil can be done via ultra turrax mixer (10 000 rpm), under a flow of nitrogen to avoid oxidation. Suitable oils include but are not limited to saturated and unsaturated fats and oils, for instance sunflower oil, high oleic sunflower oil, canola, cottonseed oil, corn/maize oil, Linola™, rapeseed oil, olive oil, soybean oil, palm oil, palm kernel oil, coconut, fish oil, linseed oil, peanut/groundnut oil, safflower oil, sesame oil, butter, lard, cocoa butter. Preferably, *Hoodia* plant extract is dissolved in medium chain-length tri-acyl-glycerides (MCT) rich oils, mono-acyl-glycerides rich oils or di-acyl-glycerides rich oils or mixtures thereof, because of the high solubility of steroidal glycosides in these oils.

MCT is obtained as a condensation reaction product of three moles of fatty acid (comprising from 6 to 14 carbon atoms) with one mole of glycerol. Preferred MCTs include but are not limited to: Miglyol 808 (MCT Oil) (Tricaprylin); Miglyol 810 (MCT Oil)(Caprylic/Capric Triglyceride); Miglyol 812 (MCT Oil)(Caprylic/Capric Triglyceride); Miglyol 818 (Caprylic/Capric/Linoleic Triglyceride); Miglyol 829 (Caprylic/Capric/Succinic Triglyceride).

Suitable fatty acids that may be used to obtain MCT include saturated or unsaturated fatty acids comprising from 6 to 14 carbon atoms, preferably from 6 to 12 carbon atoms.

Examples of suitable fatty acids include but are not limited to:

| | | | |
|---|---|---|---|
| Butyric | (butanoic acid): | $CH_3(CH_2)_2COOH$ | C4:0 |
| Caproic | (hexanoic acid): | $CH_3(CH_2)_4COOH$ | C6:0 |
| Caprylic | (octanoic acid): | $CH_3(CH_2)_6COOH$ | C8:0 |
| Capric | (decanoic acid): | $CH_3(CH_2)_8COOH$ | C10:0 |
| Lauric | (dodecanoic acid): | $CH_3(CH_2)_{10}COOH$ | C12:0 |
| Myristic | (tetradecanoic acid): | $CH_3(CH_2)_{12}COOH$ | C14:0 |
| Myristoleic acid: | 9-tetradecenoic acid | $CH_3(CH_2)_3CH=CH(CH_2)_7COOH$ | C14:1 |

The medium-chain fatty acid fraction used commercially is mainly comprised of the eight carbon caprylic or octanoic acid and the 10 carbon capric or decanoic acid. There are much smaller amounts of the six carbon caproic or hexanoic acid and the 12 carbon lauric acid in the commercial products. The caprylic- and capric-rich mixture is finally re-esterified to glycerol to produce medium-chain triglycerides that are mainly glycerol esters of caproic ($C_6$) caprylic ($C_8$), capric ($C_{10}$) and lauric acid ($C_{12}$) in a ratio of approximately 2:55:42:1.

A continuous or batch process may be employed. For a batch process, the solution is heated for a period of time from 0.5 to 10 hours, preferably from 1 to 5.0 hours. For a continuous process (the preferred option on industrial scale) the residence times will be much shorter, e.g. typically between 10 and 15 minutes.

The resulting improved flavor extract is dissolved in the solvent, e.g. oil, used for distillation. The extract dissolved in oil may be used as such, i.e. as a food stock composition to be incorporated into food compositions, which is a preferred method, for optimum commercial-scale ease and cost, or the solvent may be removed. This can be achieved, for example, by liquid/liquid extraction, or re-crystallization, or (zone-) crystallization.

Steroidal glycoside concentration in the solution of an improved flavor extracts in oil is primarily determined by their concentration in the initial *Hoodia* extract and on the solubility of initial *Hoodia* extracts in a non-volatile solvent, in order to obtain the improved flavor extract. Generally the concentration (in the solution of improved flavor extract in oil) is from 1 to 40%, preferably, in order to obtain a true solution of steroidal glycosides in oil from 2% to 30%, more preferably from 3% to 25%, and most preferably from 5% to 20%.

The improved flavor extract may include other optional ingredients, e.g. some of the ingredients mentioned below suitable for food compositions.

Edible Food Compositions

The inventive compositions include steroidal glycosides from *Hoodia* plant extracts, ("*Hoodia* steroidal glycosides") and substantially reduced (if any) amounts of negative flavor compounds. The preferred product format of the edible appetite suppressant product is a unit serving drink or bar. A bar weight is from 20 to 100 g, preferably from 25 to 75 g, most preferably from 25 to 60 g. A drink has a volume of 80 to 600 ml, preferably 90 to 400 ml, most preferably from 100 to 350 ml. Preferably each unit serving is separately packaged and includes instructions, in particular recommendation of the number of the particular unit serving to be consumed per day.

Unit serving products of the invention contain from 50 to 4000 mg steroidal glycosides, preferably from 70 to 3000 mg, more preferably from 80 to 2000 mg, and optimally from 90 to 1500 mg.

The exact amount of the extract depends on the purity of the extract (i.e., the concentration of steroidal glycosides in the extract).

Typically then the compositions include from 0.001% to 5% of *Hoodia* steroidal glycosides, more preferably from 0.01% to 4%, most preferably from 0.05% to 3%, optimally from 0.1% to 2% (based on the extract preferably containing at least 70% of steroidal glycosides), to attain optimum balance between the amount of steroidal glycosides and the amount of a typical solvent (oil) co-present in the improved flavor extract.

In a preferred embodiment in the improved flavor extracts the ratio 3-methyl-butanoic acid to steroidal glycosides (μg compound/g steroidal glycosides) is 0-60, more preferably 0-20 and most preferably 0-10, at a steroidal glycoside concentration of at least 10% of steroidal glycosides, by weight of the extract, preferably at least 25% of steroidal glycosides, more preferably at least 50%, most preferably at least 75% and optimally at least 80%, generally up to 99%, calculated on the dried final product. In such flavor extracts, it may be preferred that the ratio 2-methoxy-phenol to steroidal glycosides (μg compound/g steroidal glycosides) is 0-0.5, more preferably 0-0.3, most preferably 0-0.2, and/or it may also be preferred that in such flavor extracts the ratio beta-ionone to steroidal glycosides (μg compound/g steroidal glycosides) is 0-0.3, more preferably 0-0.1, most preferably 0-0.05, and/or it may also be preferred that in such flavor extracts the ratio of 3-methyl-2,4-nonadione to steroidal glycosides (μg compound/g steroidal glycosides) is 0-0.2, more preferably 0-0.1, most preferably 0-0.05, and/or it may also be preferred that in such flavor extracts the ratio and 1-octene-3-one to steroidal glycosides (μg compound/g steroidal glycosides) is 0-8, more preferably 0-3, most preferably 0-1.

The unit serving products of the invention preferably contain from 50 to 4000 mg steroidal glycosides, preferably from 70 to 3000 mg, more preferably from 80 to 2000 mg, and optimally from 90 to 1500 mg. In such unit serving products it may be preferred that the ratio 3-methyl-butanoic acid to steroidal glycosides (μg compound/g steroidal glycosides) is 0-60, more preferably 0-20 and most preferably 0-10. In such unit serving products, it may be preferred that the ratio 2-methoxy-phenol to steroidal glycosides (μg compound/g steroidal glycosides) is 0-0.5, more preferably 0-0.3, most preferably 0-0.2, and/or it may also be preferred that in such unit serving products the ratio beta-ionone to steroidal glycosides (μg compound/g steroidal glycosides) is 0-0.3, more preferably 0-0.1, most preferably 0-0.05, and/or it may also be preferred that in such unit serving products the ratio 3-methyl-2,4-nonadione to steroidal glycosides (μg compound/g steroidal glycosides) is 0-0.2, more preferably 0-0.10, most preferably 0-0.05, and/or it may also be preferred that in such unit serving products the ratio of 1-octene-3-one to steroidal glycosides (μg compound/g steroidal glycosides) is 0-8, more preferably 0-3, most preferably 0-1.

Typically then the compositions include from 0.001% to 5% of *Hoodia* steroidal glycosides, more preferably from 0.01% to 4%, most preferably from 0.05% to 3%, optimally from 0.1% to 2% (preferably, from the improved flavor extract preferably containing at least 70% of steroidal glycosides), to attain optimum balance between the amount of steroidal glycosides and the amount of a typical solvent (oil) co-present in the improved flavor extract, and in which cases in the improved flavor extracts the ratio 3-methyl-butanoic acid to steroidal glycosides (μg compound/g steroidal glycosides) is 0-60, more preferably 0-20 and most preferably 0-10. In such compositions, it may be preferred that the ratio 2-methoxy-phenol to steroidal glycosides (μg compound/g steroidal glycosides) is 0-0.5, more preferably 0-0.3, most preferably 0-0.2, and/or it may also be preferred that in such compositions the ratio beta-ionone to steroidal glycosides (μg compound/g steroidal glycosides) is 0-0.3, more preferably 0-0.1, most preferably 0-0.05, and/or it may also be preferred that in such compositions the ratio 3-methyl-2,4-nonadione to steroidal glycosides (μg compound/g steroidal glycosides) is 0-0.2, more preferably 0-0.10, most preferably 0-0.05, and/or it may also be preferred that in such compositions the ratio and 1-octene-3-one to steroidal glycosides (μg compound/g steroidal glycosides) is 0-8, more preferably 0-3, most preferably 0-1. In the compositions of this paragraph, it may be preferred that an optimum balance between the amount of proteins and steroidal glycoside amount is maintained, in the range of from 0.5:1 to 200:1 (mg protein:mg steroidal glycoside), preferably from 2:1 to 100:1, most preferably from 5:1 to 75:1.

Optional Ingredients

The inventive composition (oil compositions and/or emulsions) preferably include proteins, additional fats/oils, and carbohydrates.

Suitable proteins include but are not limited to milk and milk derived proteins, egg and egg derived proteins, plant or vegetable and plant or vegetable derived proteins, soy and soy derived proteins, meat or fish and meat or fish derived proteins, cereal and cereal derived proteins, as well as combinations thereof. Examples include but are not limited to milk, skimmed milk, fat free milk, condensed milk, fermented milk, cream, whey, yoghurt, cheese, egg, buttermilk, milk powder, buttermilk powder, cream powder, whey powder, yoghurt powder, cheese powder, egg powder, calcium and sodium caseinates, lactose free dairy proteins, soy proteins, isolated soy proteins, vegetable proteins, meat and fish derived proteins, gelatin, albumin powder, and mixtures thereof.

In the most preferred embodiment of the invention, an optimum balance between the amount of proteins and steroidal glycoside amount is maintained, in the range of from 0.5:1 to 200:1 (mg protein:mg steroidal glycoside), preferably from 2:1 to 100:1, most preferably from 5:1 to 75:1.

Suitable carbohydrates include but are not limited to potato, pasta, wheat, corn, soy fiber, fruit fiber (e.g. apple and orange), sucrose, fructose, dextrose, lactose, maltodextrins, honey, corn syrup, oligofructose, starches (e.g. potato starch, corn starch, rice starch), modified starches, fruit juice, concentrated fruit juice, flours (e.g wheat, corn and rice), gums (e.g. xanthan gum, guar gum, gum arabic, locust bean gum, celluloses and modified celluloses (e.g. sodium carboxy methyl cellulose, microcrystalline cellulose, powdered cellulose), carageenan, potassium carageenan, alginates (e.g. sodium and potassium alginates), gelatin, pectin and mixtures thereof. It should be noted that some or all of the sugar may be replaced by artificial sweeteners, or artificial sweeteners may be present in addition to sugars. Artificial sweeteners include but are not limited to aspartame, cyclamates (e.g. Sodium cyclamate), acesulfame K, sucralose, saccharin, invert sugar, maltose sugar, sugar alcohols (e.g. maltitol, sorbitol) and mixtures thereof.

Suitable fats include but are not limited to saturated and unsaturated fats and oils, for instance sunflower oil, high oleic sunflower oil, canola, cottonseed oil, corn/maize oil, rapeseed oil, olive oil, soybean oil, palm oil, palm kernel oil, coconut, fish oil, linseed oil, peanut/groundnut oil, safflower oil, sesame oil, butter, lard, cocoa butter, mono- and di-acylglycerides, and mixtures thereof.

The sources of oils and fats can also be hardened (e.g. by hydrogenation) or fractionated (e.g. via solvents) and these can be mixed with other oils or fats.

Some of the fats/oil may be present in the improved flavor extract, and some may be separately added.

In order to optimise the health value of the inventive products, at least some of the fat, generally from 10 to 80%, preferably from 30 to 50%, by weight of the total fat, is present as unsaturated or polyunsaturated oil, in particular oils which contain linoleic (e.g. sunflower, soybean, corn, Linola™ or rapeseed) or linolenic acid (e.g. linseed) and mixtures thereof. Ideally the product should deliver at least 1 g per day of linoleic and/or linolenic acid, preferably from an unsaturated fat source.

To minimise the potential harmful effects, the inventive products are substantially free of trans fat, i.e. contain less then 0.5% of trans fat, preferably less then 0.1%, most preferably less than 0.05% and optimally 0% trans fat, by weight of the product.

The preferred inventive compositions include essential minerals selected from the group consisting of phosphorus, iron, zinc, copper, selenium, magnesium, manganese, molybdenum and chromium, especially iron, phosphorous and zinc, and most especially iron as these are considered essential for the nutrition and the lack of one or more of these, and especially iron, in sufficient amounts may lead to health problems. The minerals described in this paragraph are added minerals rather than the trace amounts that may be present in various raw ingredients.

The preferred ingredients to deliver these minerals include but are not limited to magnesium oxide, ferrous sulfate, ferrous lactate, ferrous fumarate, ferric pyrophosphate, ferric orthophosphate, carbonyl iron, electrolytic iron, NaFeEDTA, zinc oxide, zinc gluconate, chromium chloride, sodium selenate, manganese sulfate and mixtures thereof.

The various minerals are included in the inventive products in the amounts as follows:

| Mineral | Units | Range (per unit serving) | | Preferred range (per unit serving) | |
| --- | --- | --- | --- | --- | --- |
| | | Low | High | Low | High |
| Phosphorous | Mg | 100 | 1000 | 300 | 500 |
| Iron | Mg | 1 | 10 | 3 | 7 |
| Zinc | Mg | 1 | 7 | 2 | 6 |
| Magnesium | μg | 20 | 200 | 80 | 150 |
| Selenium | μg | 3 | 40 | 7 | 25 |
| Chromium | μg | 5 | 50 | 10 | 42 |
| Molybdenum | μg | 3 | 40 | 7.5 | 27 |
| Manganese | Mg | 0.05 | 6 | 0.2 | 1 |
| Copper | Mg | 0.1 | 2 | 0.2 | 0.6 |

In particular the range of steroidal glycosides to iron is from 25:1 to 500:1 (mg steroidal glycosides:mg iron), preferably from 40:1 to 400:1, most preferably 50:1 to 300:1.

The inventive composition preferably further includes additional nutrients, vitamins and additional minerals to deliver healthy nutrition, despite the appetite suppression. Suitable vitamins and minerals, include but are not limited to Vitamin A, Vitamin D, Vitamin E, Vitamin C, Thiamin, Riboflavin, Niacin, Vitamin B6, folate, Vitamin B12, Biotin, Pantothenic acid, Calcium, Potassium, Sodium, iodine, vitamin K, and mixtures thereof.

The preferred ingredients to deliver vitamins and minerals include but are not limited to potassium phosphate, calcium phosphate, magnesium oxide, magnesium phosphate, ascorbic acid, sodium ascorbate, vitamin E acetate, niacinamide, ferric orthophosphate, calcium pantothenate, zinc oxide, zinc gluconate, vitamin A palmitate, pyridoxine hydrochloride, riboflavin, thiamin mononitrate, biotin, folic acid, chromium chloride, potassium iodide, sodium molybdate, sodium selenate, phytomenadione (vitamin K), cholecalciferol (vitamin D3), cyanocobalamin (vitamin B12), manganese sulfate and mixtures thereof. Preferably, the inventive product contains at least 10% or more of the recommended daily amount ("RDA") of the vitamins and minerals.

Another especially preferred optional ingredient is fiber. Suitable fiber sources include but are not limited to: inulin/oligofructose, gum arabic, cellulose, cellulose gum, wheat fiber (nutriose), fruit pulp/fiber, pectin, guar gum. Fiber is included generally in an amount of from 0.5-10 g per product, preferably 0.8 to 8, most preferably from 1 to 5.

The inventive products may further include meat, fish, meat and fish extracts, fruit, dried fruit, fruit concentrates, fruit extracts, fruit juices, tea (e.g. green tea) vegetables, vegetable extracts and concentrates, nuts, nut extracts, chocolate, bread, vinegar, salt, pepper, cocoa powder, herbs (e.g. parsley), herb extracts, spices (e.g. cinnamon), spice extracts, emulsifiers, acidity regulators (e.g. phosphoric, malic, maleic, citric, tartaric acids and salts thereof), flavonoids, preservatives (e.g. lactic acid, EDTA, tocopherols, sodium benzoate), colors (e.g. beta carotene, lycopene, caramel, carmine red), fibers (e.g. soy), leavening agents (e.g., sodium bicarbonate), pectin, citric acid, yeast, salt, glycerine, and mixtures thereof.

The preferred inventive products are substantially free of cholesterol, i.e. the products comprise less than 10 mg of cholesterol, preferably no more than 5 mg per unit serving, and optimally are free of cholesterol. The preferred products include phyto-sterols and/or phyto-stanols for cholesterol lowering effects.

The preferred inventive products comprise less than 6 g of sodium, preferably less than 3 g, most preferably less than 1 g, optimally less than 150 mg per unit serving.

The preferred inventive products contain at least 70 mg of potassium, preferably at least 100 mg, most preferably at least 140 mg per unit serving.

The final products according to the invention may be in solid or liquid form. The liquid products according to the invention are preferably oil-in-water emulsions wherein the steroidal glycoside containing plant extracts are dissolved in an oil phase.

The especially preferred unit serving drink according to the invention has the following composition, in addition to the steroidal glycoside:
75-95 wt % (preferably 80-90 wt %) moisture
0.5-10 wt % (preferably 1-7 wt %) protein
0.5-6 wt % (preferably 0.6-5 wt %) fat (including the oils of the inventive oil composition)
3-20 wt % (preferably 4-15 wt %) carbohydrate and
up to 8 wt % (preferably 1-6 wt %) minor components The especially preferred unit serving bar according to the invention has the following composition, in addition to the steroidal glycoside:
3-30 wt % (preferably 5-25 wt %) moisture
3-30 wt % (preferably 5-25 wt %) protein
3-30 wt % (preferably 5-25 wt %) fat (including the oils of the inventive oil composition)
35-80 wt % (preferably 40-75 wt %) carbohydrate and
up to 12 wt % (preferably 1-10 wt %) minor components Method of Use The inventive product is used for suppressing appetite and/or controlling obesity in humans. Generally, at least one inventive product should be ingested per day, typically from 1 to 5 per day (per 24 hours), until reaching the desired weight, and then continuing with this regime to maintain the desired weight. Most preferably, from 1 to 3 products are consumed per day for optimum effect. Most preferably, the inventive products are consumed for at least 14 consecutive days.

While the above summarizes the present invention, it will become apparent to those skilled in the art that modifications, variations and alterations may be made without deviating from the scope and spirit of the present invention as described and claimed herein. The invention will now be further illustrated in the following non-limiting examples.

EXAMPLE 1

In this example, the character impact components of the off-flavor of *Hoodia* extract were identified. Initial *Hoodia* extract (outside the scope of the invention), containing approximately 80% (w/w) steroidal glycosides, was obtained via the following steps: harvesting and maceration of the plant, air-drying, extraction with methanol, washing with n-heptane, extraction with a mixture of n-heptane and methyl-ethyl-ketone, and vacuum-drying. This was a liquid/liquid extraction described in US 2008/0044552.

The extract was dissolved at a concentration of 10% (w/w) in medium-chain tri-acyl-glyceride oil, Ester-610 (Chempri BV, Oleochemicals, Raamsdonksveer, NL), steamed at 180 degr C. for 5 hours before use. 100 g of this oil solution was subjected for five hours to high-vacuum degassing (HVD), at a temperature of 60° C. and a vacuum of $1.7 \times 10^{-6}$ bar. Volatiles were trapped in a U-shaped tube placed in liquid nitrogen. After degassing, the tube was disconnected and rinsed with 2 mL of ethyl ether. The flavor of the distillate (the volatiles that were collected) was evaluated by means of smelling strips and compared to that of the oil solution. It was concluded that the distillate flavor was representative of the flavor of the initial *Hoodia* extract, characterized by a hay/tobacco flavor, combined with spicy/medicinal notes, and a sweaty after-smell.

The distillate was analysed by gas chromatography—olfactory/mass spectrometry (Agilent 6890 GC-5973 MSD system equipped with a Gerstel ODP-3 sniff port) on two columns of different polarity [FFAP and VF5-MS from Varian, column dimension 30 m*0.25 mm, df=0.25 μm]. The GC effluent was split: approximately one half was led to the mass-spectrometer, the other part to an olfactory detection port. In a series of runs, the HVD product was subjected to GC-olfactometry by five experienced assessors. The assessors attributed an intensity score to every flavor signal using a nine-point scale (1-9). The data were aligned and consolidated, leading to a frequency score (number of people perceiving the signal), an averaged intensity score, and intensity impact (the frequency score multiplied by intensity score (see table 1)).

Several signals could not be identified in the standard GC-MS set-up using Amdis deconvolution software. For that reason the sample was also analysed using a comprehensive two-dimensional GC (Agilent 6890 GC equipped with a LECO GC*GC Thermal Modulator and secondary oven), connected to a time-of-flight-MS (Leco Pegasus 4D TOF MS). This analysis was performed off-line, without parallel olfactometry, focusing on the parts of the one-dimensional chromatogram where signals were detected that could not be identified by 1D GC-MS. The type of (polar) column used for the first dimension was of the same type as used in GC-olfactometry. With the help of the 2D GC-MS all important odor-active compounds were identified (table 1).

1. Distillation 80° C.—1% steam ($H_2O$) stripping—5 hour (contained 12.3% *Hoodia* extract in the oil)
2. Distillation 120° C.—1% steam stripping—5 hour (contained 12.3% *Hoodia* extract in the oil)
3. Distillation 180° C.—1% steam stripping—5 hour (contained 12.5% *Hoodia* extract in the oil)
4. Short path distillation (SPD) product: *Hoodia* extract, 10% solution in Delios V (MCT oil) distilled at 100° C., 0.001 mbar
5. Initial extract, a 12% solution in di-acyl-glyceride oil (a further dilution of a factor 10 was made for the quantification of compounds of too high concentration).

TABLE 1

| Compound | Aroma description | Frequency | Intensity | Intensity Impact |
| --- | --- | --- | --- | --- |
| 3-methyl-butanoic acid | sweaty, cheesy | 5 | 8 | 40 |
| 2-methoxy-phenol (guaiacol) | medicinal | 2 | 8 | 16 |
| beta-ionone | floral (enhances hay) | 3 | 4 | 12 |
| 3-methyl-2,4-nonadione | hay, floral (*) | 5 | 7 | 35 |
| 1-octene-3-one | mushroom | 5 | 7 | 35 |
| vanillin + phenylacetic acid | vanillin, honey | 5 | 7 | 35 |
| 2-methyl-propanoic acid | sweaty | 5 | 6 | 30 |
| 5-Hydroxy-2-decenoic acid lactone | coconut, sweet | 5 | 5 | 25 |
| pantoic lactone and/or furaneol | sweet, caramellic | 4 | 6 | 24 |
| 1-hexen-e-one | plastic, solvent | 4 | 6 | 24 |
| Methyl-phenylacetate | honey | 4 | 5 | 20 |
| 1-nonen-3-one | mushroom | 4 | 3 | 12 |
| maltol | roasted, sweet | 3 | 6 | 18 |
| 2-methoxy-4-vinylphenol | clove | 3 | 6 | 18 |
| menthol | medicinal, herbal | 3 | 6 | 18 |
| hexanoic acid | animallic, herbal | 3 | 5 | 15 |
| nonadienal; (E,Z)-2,6- | cucumber | 3 | 5 | 15 |
| gamma-octalacton | coconut | 3 | 5 | 15 |
| phenylethyl alcohol | medicinal, floral | 3 | 4 | 12 |
| gamma-nonalactone | coconut, candy | 3 | 4 | 12 |
| 2-acetylfuran | cardboard, mushroom | 3 | 4 | 12 |
| methyl-phenol | camphor, medicinal | 3 | 4 | 12 |
| octadien-3-one; (Z)-1,5- | metallic | 3 | 4 | 12 |
| 1-hepten-3-one | candy | 3 | 3 | 9 |
| beta-damascenone | cooked apple | 2 | 8 | 16 |
| nonenal; (Z)-3- | cardboard | 2 | 7 | 14 |
| 2-Methyl-(E)-2-pentenoic acid | sweaty | 2 | 7 | 14 |
| butanoic acid | sweaty | 2 | 7 | 14 |
| Hydroxy-4,5-dimethyl-2(5H)-furanone; 3-{Sotolon} | bouillon | 2 | 7 | 14 |
| delta-octalacton | coconut | 2 | 6 | 12 |
| acetic acid | acetic | 2 | 6 | 12 |
| propanoic acid and/or 2-nonenal | herbs, woody | 2 | 6 | 12 |
| 4-methyl-acetophenone | herbal | 2 | 6 | 12 |

(*) GC-O data from analysis on CPsil-8 column

It can be seen from the results in Table 1 that 3-methyl-butanoic acid had the strongest impact and together with other acidic volatiles explains the sweaty note. The hay-note is well explained by 3-methyl-2,4-nonadione, together with vanillin, beta-ionone and other compounds. The overall smell of the *Hoodia* extract is well in line with the set of components found as character impact compounds.

EXAMPLE 2

This example investigated concentrations of various flavor compounds in the improved flavor extracts of the invention and the starting sample.

Starting material (the same initial extract as used in Example 1) was dissolved in di-acyl-glyceride oil, and subjected either to batch-wise steam distillation at various temperatures (samples 1-3), or short path distillation (sample 4), or not subjected to any treatment (sample 5):

Distillation/Stripping: The initial *Hoodia Gordonii* extract (the same starting material as in Example 1) was poured into a stainless steel vessel filled with di-acyl-glyceride oil. The components were mixed during 5-10 minutes by an ultra turrax mixer (10 000 rpm) under a flow of nitrogen. The oil with the *Hoodia* extract was heated, distilled and stripped in a glass deodorizer. The temperature was controlled by a calibrated thermocouple and the pressure by a 'Baratron' pressure gauge. The steam was generated by heating 'Millipore" water at 160° C. Standard heating time was 5 hours. For food-grade experiments, after the distillation/stripping step the oil was filled in a stainless steel pressure filter (nitrogen) and filtered over a plate filter (Seitz K100). Short path distillation (SPD): Short-Path Distillation is a continuous separation process working under (high) vacuum conditions. In the evaporator the starting material was heated, leading to evaporation of the volatile substances. Since there is a very short path between the evaporator surface and the condenser, there is also a very small pressure drop in the system. This allows very low operating pressures (down to 0.001 mbar). There was no stripping during distillation.

17 compounds were quantified using the external calibration method (see Table 2). In this method, the analysis of an unknown sample is compared to a standard sample having the same matrix and containing the same analyte, in known concentration. Since peak area and concentration are proportional, the concentration of the analyte can be calculated from the two peak areas and its concentration in the standard solution. Since the same analyte is in both samples, the calibration factor will be the same. Also in Table 2 the ion used for quantification is shown.

A stock solution (±1000 mg/kg) in di-acyl-glyceride oil was prepared with all 17 components. This solution was further diluted with di-acyl-glyceride oil to 100, 50, 10, 5, 1, 0.5, 0.1, 0.05, 0.01, 0.005, 0.001, 0.0005 and 0.0001 mg/kg.

TABLE 2

| nr. | component | Target ion |
|---|---|---|
| 1 | 2-methoxy-phenol | 124 |
| 2 | Furaneol | 128 |
| 3 | phenylacetic acid | 136 |
| 4 | Maltol | 126 |
| 5 | beta-ionone | 177 |
| 6 | 2-phenylethanol | 122 |
| 7 | beta-damascenone | 121 |
| 8 | 3-methylbutanoic acid | 60 |
| 9 | Butanoic acid | 60 |
| 10 | methylphenylacetate | 150 |
| 11 | 3-methyl-2,4-nonadione | 99 |
| 12 | massoia lacton | 97 |
| 13 | 2,6-nonadienal | 70 |
| 14 | gamma-octalacton | 85 |
| 15 | gamma-nonalacton | 85 |
| 16 | 1-octene-3-one | 70 |
| 17 | Vanilline | 152 |

Measurements

All samples were analysed on the Leco comprehensive GC*GC-TOFMS system. A reversed column set (polar→non polar) was used. The column flow (1 ml/min, pressure program calculated by the ChromaTof software) used was set optimal for the separation in the second dimension. The TOF MS was tuned using a standard auto tune and the detector was set to 1800 V for maximal sensitivity. Headspace SPME (PDMS fiber) was used as on-line extraction method.

| GC*GC conditions | |
|---|---|
| GC: | Agilent 6890 GC (equipped with a LECO GC*GC Thermal Modulator and secondary oven) |
| Primary column: | Restek StabilWax-DA 30 m * 0.25 mm, df = 0.25 μm |
| Secondary column: | SGE BPX-35 1.5 m * 0.1 mm, df = 0.1 μm |
| Carrier gas: | helium, 1 ml/min [172 kPa (2 min)-1.8 kPa/min-294 kPa (10 min)] |
| Mode: | splitless |
| Splitless time: | 1 minute |
| Primary oven program: | 35° C. (2 min)-3° C.-240° C. (10 min) |
| Secondary oven program: | 40° C. (2 min)-3° C.-245° C. (5 min) |
| Modulator temp. offset: | 30° C. (above primary oven) |
| Modulation time: | 3 sec |
| Injector: | Agilent split/splitless |
| Injector temp.: | 250° C. |
| Liner type: | SPME liner |
| TOF MS-conditions | |
| TOF: | Leco Pegasus 4D TOF MS |
| Ionisation: | EI (70 eV) |
| Source Temperature: | 200° C. |
| Mass range: | 33-250 amu |
| Acquisition rate: | 100 spectra/sec |
| Detector voltage: | 1800 V |
| Transfer line temp.: | 250° C. |
| SPME conditions | |
| Autosampler: | CTC Combi-Pal |
| Mode: | headspace |
| Vials: | 10 ml |
| Sample amount: | 2 g |
| Tray: | cooled, 5° C. |
| Incubation temp.: | 60° C. |
| Incubation time: | 3 min |
| Agitator speed: | 250 rpm |
| Agitator on time: | 5 s |
| Agitator off time: | 2 s |
| Vial penetration: | 22 mm |
| Extraction time: | 30 min |
| Injection penetration: | 54 mm |
| Desorption time: | 6 min |
| Fiber: | PDMS (100 μm, red hub) |

The results that were obtained are summarised in Table 3. The concentrations including the standard deviation (average of 3 measurements) are given in μg/kg. The analysis was performed on extracts dissolved in oil. The data are expressed, however, as concentrations in the *Hoodia* extract, without oil.

TABLE 3

| | SAMPLE 1 (80° C.) | | SAMPLE 2 (120° C.) | | SAMPLE 3 (180° C.) | | SAMPLE 4 (SPD) | | INITIAL EXTRACT | |
|---|---|---|---|---|---|---|---|---|---|---|
| Component | avg | std | avg | std | avg | std | avg | std | avg | std |
| 3-methylbutanoic acid | 2232 | 576 | 1152 | 136 | 2048 | 288 | 10380 | 550 | 464560 | 10080 |
| 2-methoxy-phenol | 304 | 96 | 64 | 16 | 8 | 0 | 120 | 10 | 2200 | 288 |
| beta-ionone | 1176 | 80 | 0 | 0 | 0 | 0 | 1680 | 40 | 2000 | 64 |
| 3-methyl-2,4-nonadione | 104 | 40 | 32 | 8 | 0 | 0 | 90 | 0 | 1208 | 344 |
| 1-octene-3-one | 1880 | 80 | 96 | 16 | 448 | 112 | 5090 | 250 | 27208 | 2840 |
| Maltol | 1968 | 640 | 280 | 64 | 344 | 200 | 2500 | 250 | 59000 | 3664 |
| 2-phenylethanol | 264 | 72 | 64 | 8 | 24 | 8 | 720 | 50 | 9448 | 264 |
| beta-damascenone | 376 | 24 | 0 | 0 | 0 | 0 | 210 | 0 | 2072 | 8 |
| methylphenylacetate | 32 | 8 | 0 | 0 | 0 | 0 | 160 | 0 | 2840 | 24 |
| massoia lacton | 9368 | 880 | 16 | 8 | 128 | 24 | 4510 | 270 | 10160 | 328 |
| 2,6-nonadienal | 64 | 8 | 8 | 0 | 0 | 0 | 0 | 0 | 392 | 8 |

TABLE 3-continued

| Component | SAMPLE 1 (80° C.) avg | std | SAMPLE 2 (120° C.) avg | std | SAMPLE 3 (180° C.) avg | std | SAMPLE 4 (SPD) avg | std | INITIAL EXTRACT avg | std |
|---|---|---|---|---|---|---|---|---|---|---|
| gamma-octalacton | 176 | 16 | 48 | 8 | 40 | 0 | 580 | 20 | 896 | 32 |
| gamma-nonalacton | 792 | 80 | 88 | 8 | 72 | 8 | 780 | 0 | 1384 | 16 |
| Vanillin | 168792 | 43552 | 896 | 168 | 992 | 360 | 85390 | 2810 | 258904 | 1688 |

Table 4 shows the weight ratio of the primary and secondary off-flavor compounds to the steroidal glycosides (micrograms per gram) in the samples, as can be calculated from the data of table 3 and the steroidal glycoside content of the starting material of 80% w/w.

TABLE 4

| Component | SAMPLE 1 80° C. avg | SAMPLE 2 120° C. avg | SAMPLE 3 180° C. avg | SAMPLE 4 SPD avg | INITIAL EXTRACT avg |
|---|---|---|---|---|---|
| 3-methylbutanoic acid | 2.8 | 1.4 | 2.5 | 12.5 | 560 |
| 2-methoxy-phenol | 0.38 | 0.077 | 0.010 | 0.14 | 2.6 |
| beta-ionone | 1.5 | 0 | 0 | 2.0 | 2.4 |
| 3-methyl-2,4-nonadione | 0.13 | 0.038 | 0 | 0.11 | 1.5 |
| 1-octene-3-one | 2.3 | 0.12 | 0.54 | 6.1 | 32 |

It can be seen from the results in Tables 3 and 4 that, compared to the initial *Hoodia* extract, all samples subjected to distillation (1, 2, 3 and 4) had significantly reduced levels of the negative flavor compounds. Samples 1, 2, and 3 which were subjected to the distillation/stripping had substantially lower levels of the negative flavor compounds, compared to Sample 4 obtained by short path distillation, with sample 2 (120° C.) having the lowest levels. Sample 1, treated at 80° C. shows a decrease in the concentration of the off-flavor components when compared with the starting material, but the residual levels were higher than at the higher temperatures. The difference in efficacy of off-flavor removal between 120 and 180° C. was minimal, but higher temperatures lead to degradation of some of the steroidal glycosides. Removal of beta-ionone, 3-methyl-2,4-nonadione and 1-octene-3-one was especially impacted by temperature, with temperatures above 80° C. more preferred, achieving more preferred levels of negative flavor compounds.

The analytical data were well in line with the tasting results. The five samples were tasted by a panel (5 to 7 panellists). For this, the oil samples containing an improved flavor *Hoodia* extract were diluted 1:1 with sunflower oil. Smell was evaluated by sniffing at the opening of the bottle containing the diluted samples. Subsequently, a small amount was pipetted on a plastic tea spoon and tasted. All panellists agreed that samples 1 and 4 were considerably improved in flavor when compared to the starting material. Samples 2 and 3, according to the panel, were both essentially free of off-flavor.

EXAMPLE 3

The following appetite suppressant Muesli Bar, Yoghurt Muesli Variant, is within the scope of the invention:

| Formulation: | |
|---|---|
| Ingredient | Formula |
| Maltitol | 4.4 |
| Glucose syrup | 8.4 |
| Polydextrose syrup | 13.3 |
| Inulin syrup | 5.6 |
| Coconut oil | 1.0 |
| MCT oil (e.g. Delios V) | 2.9 |
| Brown Sugar | 1.0 |
| Lecithin | 0.6 |
| Pectose paste | 5.0 |
| Glycerine | 5.0 |
| Date paste | 3.0 |
| Flavorings | 0.4 |
| Colouring | 0.1 |
| Oatflakes | 3.7 |
| Coconut flakes | 1.9 |
| Apple Fiber | 3.9 |
| Soy Nuggets | 31.1 |
| Vitamin & Mineral Premix | 3.9 |
| Yogurt Coating | 10.0 |
| Improved Flavor *Hoodia* Plant Extract (80% steroidal glycosides) | 0.42 |
| Water loss during manufacture | −5.7 |
| TOTAL | 100.0 |

Nutritional Info:
Product weight as consumed: 60 g

| Vitamins | Per 100 g | Per 60 g Bar |
|---|---|---|
| Vitamin A (µg) | 380.0 | 228.0 |
| Vitamin D (µg) | 3.3 | 2.0 |
| Vitamin E (mg) | 6.7 | 4.0 |
| Vitamin C (mg) | 30.0 | 18.0 |
| Thiamin (mg) | 0.8 | 0.5 |
| Riboflavin (mg) | 0.8 | 0.5 |
| Niacin (mg) | 10.3 | 6.2 |
| Vitamin B6 (mg) | 1.0 | 0.6 |
| Folic Acid (µg) | 140.0 | 84.0 |
| Vitamin B12 (µg) | 1.5 | 0.9 |
| Biotin (mg) | 0.05 | 0.03 |
| Pantothenic Acid (mg) | 2.7 | 1.6 |

-continued

| Minerals | | |
|---|---|---|
| Calcium (mg) | 368.0 | 220.8 |
| Phosphorus (mg) | 534.0 | 320.4 |
| Iron (mg) | 9.6 | 5.8 |
| Magnesium (mg) | 90.0 | 54.0 |
| Zinc (mg) | 5.7 | 3.4 |
| Iodine (µg) | 70.0 | 42.0 |
| Potassium (mg) | 833.3 | 500.0 |
| Copper (mg) | 0.7 | 0.4 |
| Selenium (µg) | 32.5 | 19.5 |
| Manganese (mg) | 0.7 | 0.4 |

EXAMPLE 4

The following appetite suppressant Chicken & Mushroom Soup is within a scope of the invention:

Formulation:

| Ingredient | % Formula |
|---|---|
| Water | To 100% |
| Skimmed Milk Powder | 1.2 |
| Sodium Phosphate | 0.1 |
| MCT oil (e.g. Miglyol 810) | 0.9 |
| Propylene glycol monolaurate | 0.1 |
| Butter Concentrate | 0.5 |
| Wheat Flour | 2.0 |
| Modified Maize Starch | 1.6 |
| Flavorings | 0.6 |
| White Pepper | 0.01 |
| Mace Powder | 0.007 |
| Maltodextrin | 2.8 |
| Titanium Dioxide | 0.2 |
| Garlic Powder | 0.03 |
| Onion Powder | 0.03 |
| Gelatine | 3.2 |
| Salt | 0.4 |
| MSG | 0.3 |
| Vitamin & Mineral | 0.9 |
| Parsley | 0.4 |
| Chicken Meat | 10.5 |
| Mushrooms | 4.5 |
| Cream | 0.8 |
| Improved Flavor *Hoodia* Plant Extract (80% steroidal glycosides) | 0.1 |
| TOTAL | 100.0 |

Nutritional Info:
Product weight as consumed: 295 ml

| | Per 100 ml | Per 295 ml |
|---|---|---|
| Vitamins | | |
| Vitamin A (µg) | 92.5 | 273.0 |
| Vitamin D (µg) | 0.7 | 2.0 |
| Vitamin E (mg) | 1.3 | 3.9 |
| Vitamin C (mg) | 9.2 | 27.0 |
| Thiamin (mg) | 0.1 | 0.4 |
| Riboflavin (mg) | 0.2 | 0.6 |
| Niacin (mg) | 2.2 | 6.5 |
| Vitamin B6 (mg) | 0.2 | 0.5 |
| Folic Acid (µg) | 24.4 | 72.0 |
| Vitamin B12 (µg) | 0.2 | 0.5 |
| Biotin (mg) | 0.002 | 0.005 |
| Pantothenic Acid (mg) | 0.4 | 1.1 |

-continued

| Minerals | | |
|---|---|---|
| Calcium (mg) | 85.4 | 252.0 |
| Phosphorus (mg) | 96.6 | 285.0 |
| Iron (mg) | 2.0 | 5.8 |
| Magnesium (mg) | 18.3 | 54.0 |
| Zinc (mg) | 1.2 | 3.4 |
| Iodine (µg) | 15.9 | 47.0 |
| Potassium (mg) | 186.4 | 550.0 |
| Copper (mg) | 0.1 | 0.4 |
| Selenium (µg) | 6.7 | 19.8 |
| Manganese (mg) | 0.1 | 0.4 |

EXAMPLE 5

The following appetite suppressant Strawberry Milk Drink is within the scope of the invention:

Formulation:

| Ingredient | % Formula |
|---|---|
| Skim Milk | 75.3 |
| Water | To 100% |
| Sucrose | 6.6 |
| Gum Arabic | 1.5 |
| Milk Protein | 1.6 |
| MCT oil (e.g. Delios V) | 0.75 |
| Flavoring | 0.2 |
| Colouring | 0.09 |
| Vitamin & Mineral Premix | 0.2 |
| Improved Flavor *Hoodia* Plant Extract (80% steroidal glycosides) | 0.11 |
| TOTAL | 100.00 |

Nutritional Info:
Product weight as consumed: 325 ml

| | Per 100 ml | Per 325 ml |
|---|---|---|
| Vitamins | | |
| Vitamin A (µg) | 86.0 | 279.5 |
| Vitamin D (µg) | 0.7 | 2.1 |
| Vitamin E (mg) | 1.1 | 3.6 |
| Vitamin C (mg) | 6.5 | 21.1 |
| Thiamin (mg) | 0.2 | 0.8 |
| Riboflavin (mg) | 0.2 | 0.8 |
| Niacin (mg) | 2.7 | 8.8 |
| Vitamin B6 (mg) | 0.3 | 0.9 |
| Folic Acid (µg) | 21.5 | 69.9 |
| Vitamin B12 (µg) | 0.2 | 0.6 |
| Biotin (mg) | 0.02 | 0.05 |
| Pantothenic Acid (mg) | 0.7 | 2.1 |
| Minerals | | |
| Calcium (mg) | 123.0 | 399.8 |
| Phosphorus (mg) | 80.0 | 260.0 |
| Iron (mg) | 1.7 | 5.5 |
| Magnesium (mg) | 20.0 | 65.0 |
| Zinc (mg) | 1.6 | 5.2 |
| Iodine (µg) | 16.2 | 52.7 |
| Potassium (mg) | 154.0 | 500.5 |
| Copper (mg) | 0.2 | 0.5 |
| Selenium (µg) | 7.5 | 24.4 |
| Manganese (mg) | 0.2 | 0.7 |

EXAMPLE 6

The following appetite reducing acidified dairy drink was prepared:

| Formulation: | |
|---|---|
| Ingredient | % Formula |
| Skim Milk | 6.8 |
| Water | To 100% |
| Sucrose | 5.0 |
| HM Pectin | 0.5 |
| Milk Protein | 1.6 |
| MCT oil (e.g. Delios V) | 5.0 |
| Citric acid (50% solution) | 1.3 |
| Flavoring | 0.2 |
| Acesulfame-K | 0.1 |
| Aspartame | 0.1 |
| Improved Flavor Hoodia Plant Extract (30% steroidal glycosides) | 0.5 |
| TOTAL | 100.0 |

Nutritional Info:
Product weight as consumed: 90 g

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

What is claimed is:

1. An extract of a *Hoodia* plant, the extract comprising:
   a. from about 10% to about 99% of steroidal glycosides, by weight of the extract; and
   b. 3-methylbutanoic acid,
      wherein the weight ratio of 3-methylbutanoic acid to the steroidal glycosides in micrograms/grams is from about 0 to about 60.

2. The extract of claim 1 further comprising 2-methoxy-phenol, wherein the weight ratio of 2-methoxy-phenol to the steroidal glycosides in micrograms/grams is from about 0 to about 0.5.

3. The extract of claim 1, wherein the extract further comprises beta-ionone, and wherein the weight ratio of beta-ionone to the steroidal glycosides in micrograms/grams is from 0 to about 0.25.

4. The extract of claim 1 further comprising 3-methyl-2,4-nonadione, wherein the weight ratio of 3-methyl-2,4-nonadione to the steroidal glycosides in micrograms/grams is from about 0 to about 0.14.

5. The extract of claim 1 further comprising 1-octene-3-one, wherein the weight ratio of 1-octene-3-one to the steroidal glycosides in micrograms/grams is from about 0 to about 8.

6. The extract of claim 1 wherein the extract comprises at least about 25% steroidal glycosides, by weight of the extract.

7. The extract of claim 1 wherein the extract comprises at least about 75% steroidal glycosides, by weight of the extract.

8. The extract of claim 1 wherein the *Hoodia* plant is selected from the group consisting of *Trichocaulon piliferum, Trichocaulon officinale, Hoodia currorii, Hoodia gordonii, Hoodia lugardii* and mixtures thereof.

9. The extract of claim 8 wherein the plant is *Hoodia gordonii*.

10. The extract of claim 1 wherein the steroidal glycosides comprise a compound of Formula (1):

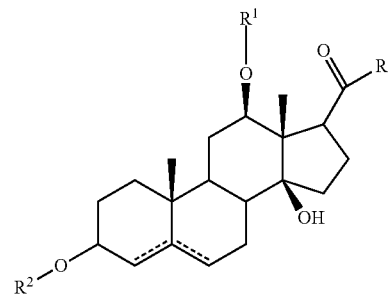

wherein

R is alkyl;

$R^1$ is H, alkyl, tigloyl, benzoyl or any other organic ester group;

$R^2$ is H, a radical consisting of one or more 6-deoxy carbohydrates, a radical consisting of one or more 2,6-dideoxy carbohydrates, glucose radical, or a radical consisting of a combination of two or more carbohydrates selected from 6-deoxy carbohydrates, 2,6-dideoxy carbohydrates, and glucose; and wherein the broken lines indicate the optional presence of a further bond between carbon atoms C4 and C5 or between carbon atoms C5 and C6.

11. A composition comprising the extract of claim 1 dissolved in a food grade oil.

12. The composition of claim 11, wherein the oil is selected from the group consisting of medium chain tri-acyl-glyceride, di-acyl-glyceride oil, mono-acyl-glyceride oil, and mixtures thereof.

13. The composition of claim 11 comprising from about 1% to about 40% of steroidal glycosides.

14. A composition comprising from about 0.001% to about 5%, by weight of the composition, of *Hoodia* steroidal glycosides, and 3-methyl-butanoic acid, wherein the weight ratio of 3-methyl-butanoic acid to the steroidal glycosides in micrograms/grams is from about 0 to about 60.

15. The composition of claim 14 further comprising 2-methoxy-phenol, wherein the weight ratio of 2-methoxy-phenol to the steroidal glycosides in micrograms/grams is from about 0 to about 0.5.

16. The composition of claim 14 further comprising beta-ionone, wherein the weight ratio of beta-ionone to the steroidal glycosides in micrograms/grams is from about 0 to about 0.25.

17. The composition of claim 14 further comprising 3-methyl-2,4-nonadione, wherein the weight ratio of 3-methyl-2,4-nonadione to the steroidal glycosides in micrograms/grams is from about 0 to about 0.14.

18. The composition of claim 14 further comprising 1-octene-3-one, wherein the weight ratio of 1-octene-3-one to the steroidal glycosides in micrograms/grams is from about 0 to about 8.

19. The composition of claim 14 which is in the form of a drink or a shake.

20. A method of suppressing appetite in a mammal, the method comprising orally administering to a mammal the composition of claim 11.

21. The extract of claim 10, wherein $R^1$ is tigloyl.

* * * * *